(12) United States Patent
De Heus

(10) Patent No.: US 6,797,233 B1
(45) Date of Patent: Sep. 28, 2004

(54) STERILIZATION APPARATUS

(75) Inventor: Evert Bastiaan De Heus, Wertkedam (NL)

(73) Assignee: Hevo N.V., Poppel (BE)

( * ) Notice: Subject to any disclaimer, the term of this patent is extended or adjusted under 35 U.S.C. 154(b) by 0 days.

(21) Appl. No.: 09/230,001

(22) PCT Filed: Jul. 9, 1997

(86) PCT No.: PCT/NL97/00404
§ 371 (c)(1),
(2), (4) Date: May 18, 1999

(87) PCT Pub. No.: WO98/02193
PCT Pub. Date: Jan. 22, 1998

(30) Foreign Application Priority Data

Jul. 12, 1996 (NL) .............................. 1003576

(51) Int. Cl.[7] .................................. A61L 2/00
(52) U.S. Cl. .................. 422/26; 422/113; 422/114; 422/116; 422/298
(58) Field of Search .................. 422/26, 298, 113, 422/114, 116

(56) References Cited

U.S. PATENT DOCUMENTS

| | | | |
|---|---|---|---|
| 4,238,447 A | * 12/1980 | Wolff | 422/26 |
| 4,263,258 A | * 4/1981 | Kalasek | 422/113 |
| 4,909,988 A | * 3/1990 | Childers et al. | 422/26 |
| 5,103,076 A | 4/1992 | Houkuwa | 219/401 |
| 5,840,248 A | * 11/1998 | Ongaro | 422/26 |

FOREIGN PATENT DOCUMENTS

| | | |
|---|---|---|
| DE | 14 92 497 | 10/1969 |
| DE | 29 25 034 A | 2/1980 |
| EP | 0 492 056 B1 | 11/1996 |
| EP | 0 889 067 A1 | 1/1999 |
| EP | 0 904 237 B1 | 3/1999 |
| WO | WO 92/01479 A | 2/1992 |

* cited by examiner

*Primary Examiner*—Krisanne Thornton
(74) *Attorney, Agent, or Firm*—Knobbe Martens Olson & Bear LLP

(57) ABSTRACT

Sterilization apparatus, for medical instruments and similar objects, which is easy to handle and/or remove and which is mainly formed by a casing (1) provided with a sterilization boiler (11) and means for performing the sterilization process. The sterilization apparatus comprises a double-walled boiler (11) whereby fluid (13), such as demineralized water, which is present between the inner wall (3) and the outer wall (12), is heated by heating elements (17, 18) so as to achieve a sable temperature of the boiler wall as well as to generate steam (16). The apparatus further comprises a water reservoir (19), pump (21) and valve (22) for supplying water to the boiler and means (23, 24) for controlling the level of water, a valve (25) through which generated steam (16) can be injected into the sterilization chamber, a water-ejector (31) for drawing a vacuum in the chamber, and an aeration valve (29) for releasing the vacuum.

16 Claims, 3 Drawing Sheets

STERILIZATION APPARATUS

This application is the U.S. National Phase under 35 U.S.C. Section 371 of International Application PCT/NL97/00404, filed Jul. 9, 1996.

The invention relates to a sterilisation apparatus for medical instruments and the like objects, which is easy to handle and/or remove and which is mainly formed by a casing provided with a sterilisation boiler and means for performing the sterilisation process.

Such a sterilisation apparatus, also called a mini sterilisation apparatus, is often used in dentists' practices. The contents of the sterilisation apparatus thereby range between 10 to 50 liters and the required temperatures often are between 121 degrees C. and 134 degrees C. at pressures of ca. 210 kPa and 310 kPa, respectively.

A problem relating to this mini sterilisation apparatus is that one can barely, if at all, comply with the (international) requirement of obtaining a stable ambient temperature of the sterilisation boiler during sterilisation.

The invention overcomes this problem since the sterilisation apparatus comprises a double-walled boiler whereby fluid such as demineralised water being present between the inner and the outer wall by which a stable temperature of the boiler wall can be achieved as well as steam generated therefrom. This makes the sterilisation process very well manageable in a relatively small sterilisation apparatus, as also shown in practice.

It is thereby advantageous that at least regulators and heating elements in said double boiler walls can provide for a stable fluid temperature.

Advantage is offered by the embodiment according to the invention in which means are present for feeding steam for the sterilisation process pulsatingly into said boiler, as well as means which can also provide a pulsating vacuum in said boiler such that air in the instruments or the like objects which are to be sterilised can be removed.

To make the sterilisation process occur automatically the sterilisation apparatus is provided with means for setting, respectively measuring pressure, temperature, time and output for controlling all phases occurring within said boiler before, during and after the sterilisation process. These means are preferably controlled by a process computer which displays various data read-outs digitally and/or alpha-numerically and/or graphically, e.g. to an internal or external printing apparatus (printer).

Especially in a dentist's practice where an autoclave will be used intensively it may be desirable to provide a mini sterilisation apparatus with a (time) switch clock for use of "stand-by" purposes, such as for heating-up of and maintaining the temperature of the boiler.

Advantage is offered by the embodiment of a mini sterilisation apparatus according to the invention which is characterized in that the sterilisation space of the boiler is provided with lateral supports for a number of standard plateaus on which instruments, whether wrapped or not, and/or bandage substances may be placed.

For effective use it is desirable that in the mini sterilisation apparatus according to the invention the front or feed side of the boiler can be sealed pressure-tight by means of a heat-isolating hinged door provided with an incorporated nut whereby the casing to that end is provided with a swivelable hermetically sealing screw. The screw seal is prefeably operated by means of an electromotor of which the operating phases are run via said process computer.

In order to comply with the procedure required of process sterilisation, according to the invention use is made of a sterilisation boiler for incorporation in a mini sterilisation apparatus which is characterized in that a cylindrical sterilisation boiler is placed symmetrically though non-concentrically within the cylindrical outer boiler, such that in the use-position the volume of the fluid or water space down in the double-walled boiler is considerably larger than up in the boiler.

It is advantageous if this sterilisation boiler is provided in a casing in which also the fluid reservoir with corresponding pump, control appendages, a dry-air connection and a connection to a vacuum line with valves being present.

The invention is hereinafter described by means of examples of embodiments, whereby advantages and other features of the invention will become apparent.

Figure 1:
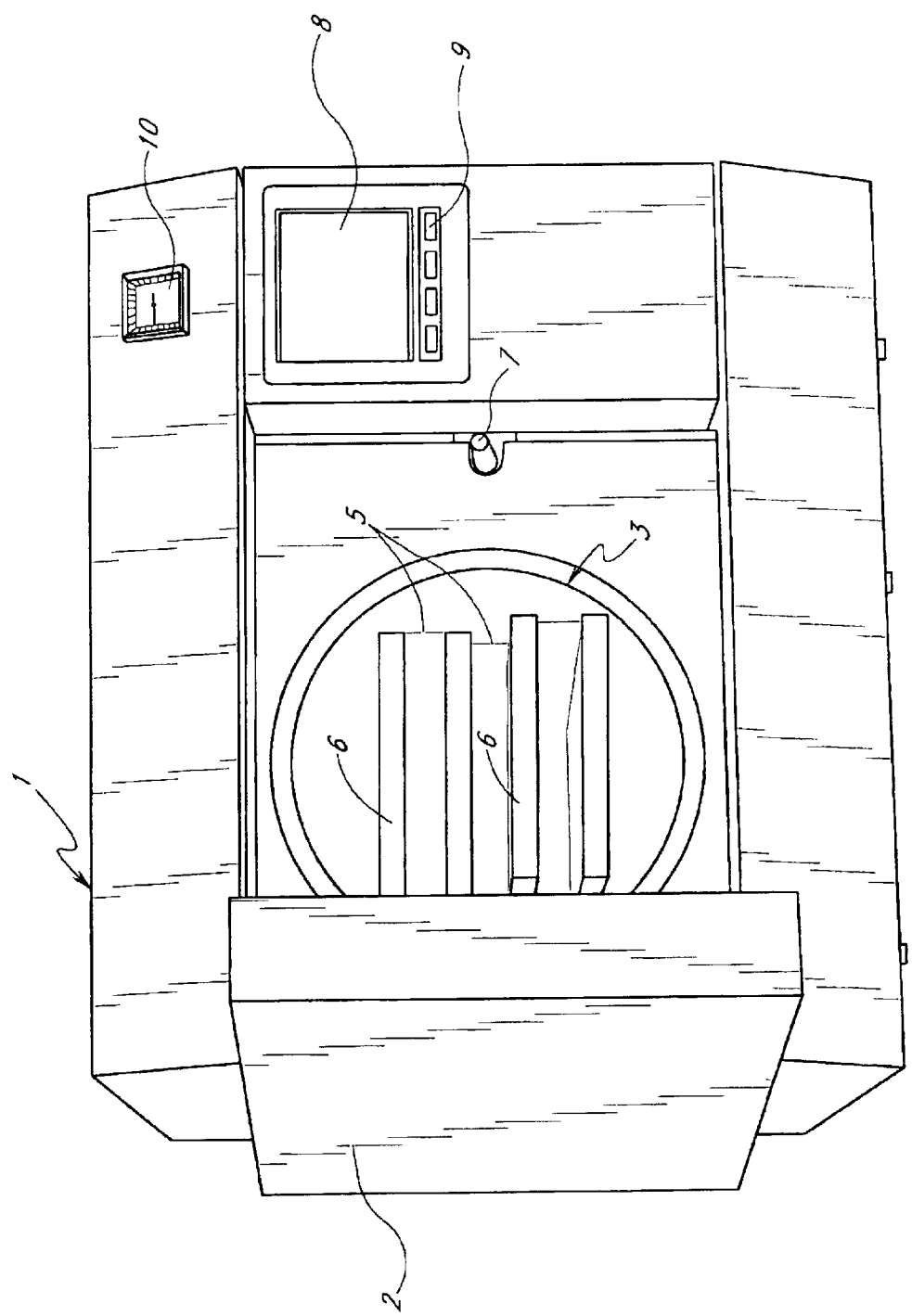
FIG. 1 shows a perspective view of a mini sterilisation apparatus.

FIG. 1 shows in perspective a front view of the sterilisation apparatus, in fact the casing 1 thereof, which has a mainly rectangular shape and is made of suitable plate material. The front side shows a door 2 which can be swivelled open over more than 120 degrees and which further is well isolated against heat loss. Opening and closing the door occur automatically by activating an electrical operating button (not drawn). The opened door depicts a (inner) boiler 3 of which the space 4 in this embodiment is provided with four bearing plateaus 6, so-called norm trays, on which (wrapped) instruments or bandage substances can be transported. To that end space 4 is provided with supports 5. Door 2, which can seal sterilisation space 4, is fixed pressure-tight in the closed position by an electrically driven screw-seal 7 and cannot be opened during a sterilisation process. During a process the LCD screen 8 graphically displays the course of this process.

The sterilisation apparatus moreover comprises a process computer of which the control 9 is embodied with an indication for each process phase. The pressure, temperature, sterilisation time, drying time and possible malfunctioning are displayed digitally, eventually supported alpha-numerically or graphically. The pressure in the so-called steam generator is, as prescribed, displayed analogously on indicator 10.

Figure 2:
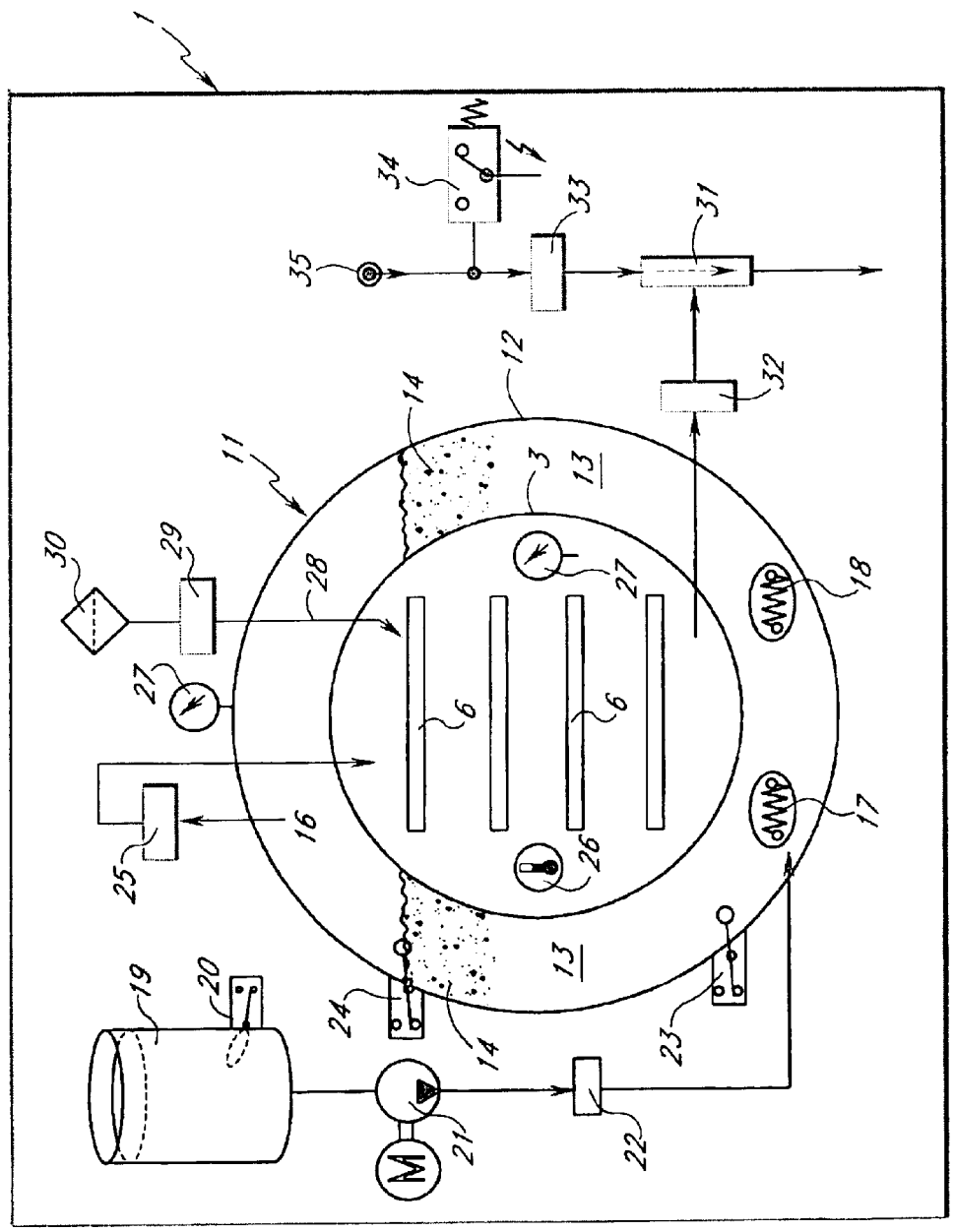
FIG. 2 shows a block scheme of the most important operational functions of the sterilisation apparatus.

FIG. 2 schematically shows the sterilisation boiler 11 with various auxiliary parts and control apparatuses, which parts are described hereinafter.

It is to be noted that similar references are used for similar parts.

Boiler 11 according to the invention comprises an inner wall and an outer wall, 3 respectively 12, whereby the contents of the inner boiler range between 10 to 50 liters. Demineralised water (demi-water) 14-added to space 13 of the double boiler wall 3, 12-is heated such that steam 16 is produced at the top of the boiler. Heating of the water occurs through heating elements 17, 18 which have been provided in boiler space 13. For the provision of water the sterilisation apparatus comprises a water reservoir 19 onto which a floating switch 20 for level control is provided. In this arrangement a feed pump 21 is applied by means of which water down in space 13 of the double boiler wall 3, 12 can be supplied. A shut-off valve 22 for pumping water for boiler space 13 is provided in the pump circuit. As already indicated above, heating elements 17, 18 are provided at the bottom of boiler 3, 12 by means of which the water supplied can be heated, such that steam 16 is formed at the top for the purpose of the sterilisation process. A safety switch 23 with a float embodiment for protection against dry-boiling is provided at the bottom of the boiler. A water level controller 24 is present at the top so that the proper ratio between steam and water is always obtained. The generated steam 16 is supplied pulsatingly from boiler space 13 through a steam valve 25 into the inner boiler 3. Further, there is a temperature measuring device 26 as well as a pressure transmitter within inner boiler 3. A similar transmitter is also provided in the outer boiler 12. In FIG. 2 the left-hand side depicts the water and steam system and the right-hand side depicts the vacuum system. Thereby a feed line 28 is provided at the top side of the boiler, in which an aeration valve 29 is provided for feeding clean air when a vacuum is prevailing in the boiler. For the sake of certainty a sterile filter 30 provides for clean air when feeding to valve 29.

According to the invention a vacuum is drawn pulsatingly in the boiler, which is achieved by using a water-ejector system which mainly comprises an ejector 31 connected to a vacuum valve 32 which is connected through a line to inner boiler 3. A cold-water valve 33 is incorporated in the water system of ejector 31 which serves for generating a vacuum through ejector 31. As seen in FIG. 2, the ejector 31 is located outside of the inner boiler 3 and outer boiler 12. Further a pressure switch 34 for measuring the water pressure is used in the line system, by which water is tapped-off from feed 35.

The following gives a brief illustration of a sterilisation process at a temperature of 134 degrees C. A process can only start if door 2 is closed, and the process begins with steaming-through whereby valves 25, 33 and 32 are opened. Valves 33 and 32 of the ejector system remain open during steaming-through. Steam valve 25 is thereby regulated at a pressure of 120 kPa within inner boiler 3. During a certain period, about 90 seconds, there is a continuous discharge of steam and air. After this period of 90 seconds steam valve 25 closes and the first vacuum pulse starts. The pulsating course of the process occurs further by successively controlling the valves concerned, the build-up of pressure as well as the time in seconds, so that the sterilisation pressure and temperature are achieved in an effective manner within the stated period. In this example a temperature of 134 degrees C. to a maximum of 137 degrees C. is achieved in about 15 seconds. Pressure control in the boiler is achieved by a autonomously functioning control process. However, in case during the sterilisation process the temperature and/or the pressure exceeds the maximum set value, the process is automatically broken off.

After the sterilisation traject drying of the objects present on plateaus 6 takes place by drawing a vacuum. To this end steam valve 25 is shut and cold-water valve 33 as well as vacuum valve 32 are opened, till a pressure of 10 kPa is reached. At this pressure the actual drying time starts, which lasts 5 minutes in this process (134 degrees C.). After drying the boiler is aerated to relieve the vacuum. If the drying process is terminated, valves 32 and 33 are shut. When the boiler pressure lies between 95–105 kPa, aeration valve 29 shuts due to which door 2 can be opened and the sterilised objects can be removed from boiler space 4.

As stated above, the whole process takes place under the control of and monitoring by a computer and the results are displayed by means of a printing device, a so-called printer (not shown).

Figure 3:
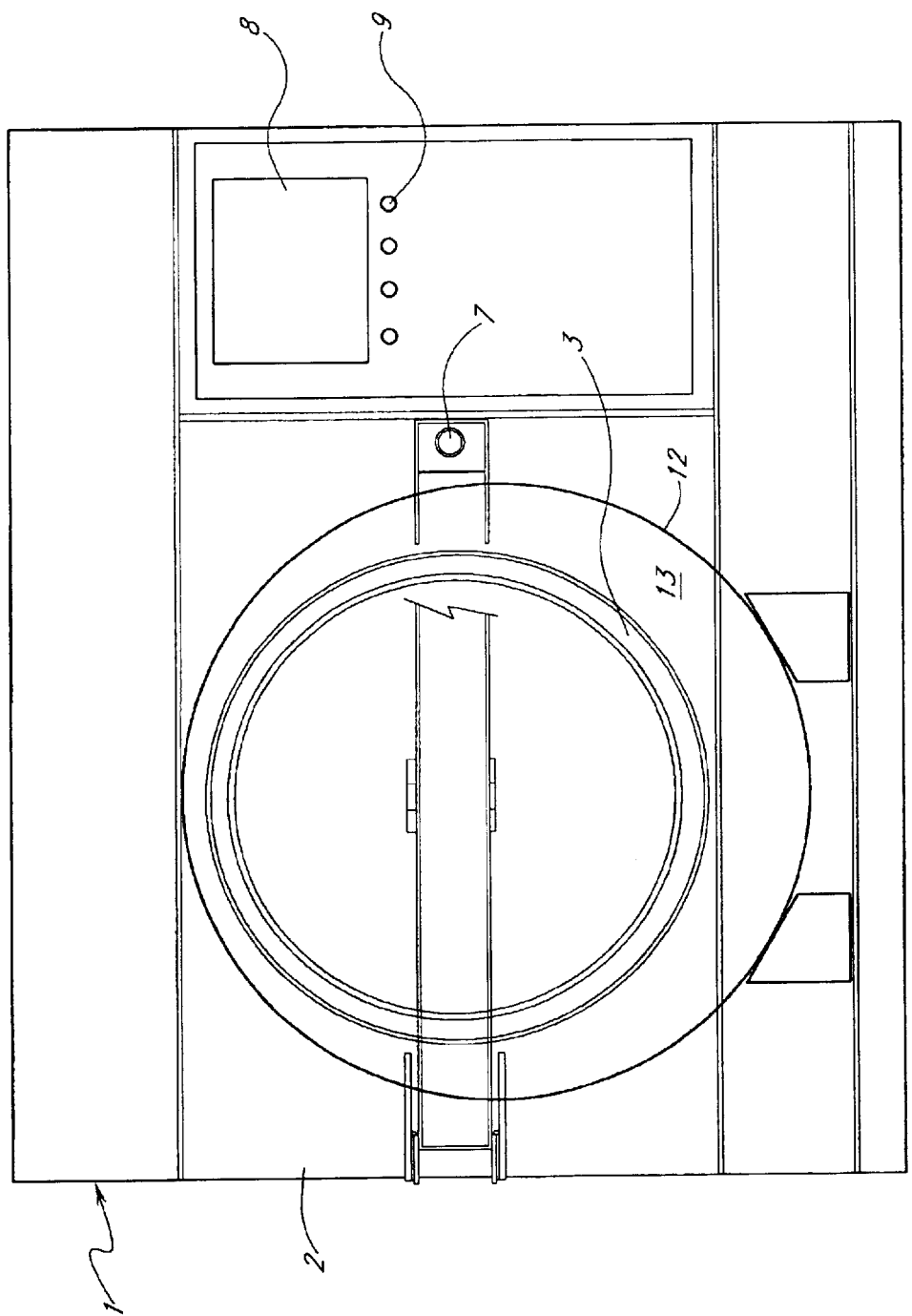
FIG. 3 shows, according to a computer drawing, another embodiment of the sterilisation apparatus.

FIG. 3 depicts another advantageous embodiment according to the invention in which in particular the water reservoir 13 has been enlarged by the positioning of inner boiler 3 relative to outer boiler 12, i.e. that the amount of water at the bottom of boiler 11 is greater than the amount at the top thereof, which may be favourable for certain sterilisation processes in view of the water-steam ratio.

The invention is not limited to the embodiments as shown and described above, since one can well imagine other arrangements of sterilisation boilers. The feature according to the invention of using a double boiler wall in a relatively small sterilisation apparatus has however resulted in the fact that such a sterilisation apparatus can comply with the highest standards, including international standards.

What is claimed is:

1. A sterilisation apparatus for medical instruments comprising a mini sterilisation apparatus, said mini sterilisation apparatus comprising a casing provided with a cylindrical double-walled sterilisation boiler having a cylindrical inner wall and a cylindrical outer wall, thereby forming an outer boiler between the inner and outer walls and an inner boiler within the inner wall, whereby water is present in the outer boiler such that a stable temperature of the inner wall can be achieved as well as steam generated therefrom, and a series of valves for providing a pulsating high vacuum in said inner boiler so as to pulsatingly feed steam into the inner boiler, said series of valves comprising a steam valve to provide steam from the outer boiler to the inner boiler and a vacuum valve connected to an ejector that comprises a cold water valve to provide a vacuum in the inner boiler, wherein the inner boiler has a volume of from about 10 to about 50 liters, and wherein the ejector is outside the inner and outer boilers.

2. The apparatus according to claim 1, further comprising regulators and heating elements in said double boiler walls which provide for a stable fluid temperature.

3. The apparatus according to claim 1, further comprising an inlet and apparatus for feeding steam for the sterilisation process pulsatingly into said boiler, and an apparatus for providing a pulsating vacuum in said boiler such that air in the instruments or the like objects which are to be sterilised can be removed.

4. The apparatus according to claim 1, further comprising an apparatus for setting and measuring pressure, temperature, time and output.

5. The apparatus according to claim 4, further comprising a process computer which displays various data read-outs digitally and/or alphanumerically and/or graphically.

6. The apparatus according to claim 1, further comprising a switch clock for "stand-by" purposes, wherein said "stand-by" purposes are for heating-up of and maintaining the temperature of said boiler.

7. The apparatus according to claim 1, further comprising lateral supports for a number of standard plateaus on which objects to be sterilised may be placed.

8. The apparatus according to claim 5, wherein the front or feed side of the boiler can be sealed pressure-tight by means of a heat-isolating hinged door provided with an incorporated nut whereby the casing to that end is provided with a swivelable hermetically sealing screw.

9. The apparatus according to claim 8, wherein said sealing screw is operated by means of an electromotor of which the operating phases are operated by said process computer.

10. The apparatus according to claim 1, wherein said cylindrical inner boiler is placed symmetrically though non-concentrically within cylindrical outer boiler, such that in the use-position the volume of the water space on the bottom of the double-walled boiler is considerably larger than at the top of the boiler.

11. The apparatus according to claim 1, wherein said cylindrical inner boiler is placed concentrically within a said cylindrical outer boiler.

12. The apparatus according to claim 5, wherein said process computer and said sterilisation apparatus are provided in a casing said casing further comprising the water reservoir with corresponding pump, control appendages, a dry-air connection and a connection to a vacuum line with valves.

13. The apparatus according to claim 1, further comprising demineralized water.

14. The apparatus according to claim 5, further comprising an internal or external printing apparatus for displaying said data read outs.

15. A method of sterilizing a medical comprising introducing the medical instrument into an apparatus according to claim 1, pulsatingly introducing said steam into said boiler, and removing said instrument from said apparatus.

16. A method according to claim 15 wherein the medical instrument comprises a hollow instrument part from which all air is removed.

* * * * *